United States Patent
Thede et al.

(10) Patent No.: US 7,137,954 B2
(45) Date of Patent: *Nov. 21, 2006

(54) DISPOSABLE NON-INVASIVE BLOOD PRESSURE SENSOR

(75) Inventors: Roger C. Thede, Afton, MN (US); Kevin R. Evans, New Richmond, WI (US)

(73) Assignee: Medwave, Inc., Danvers, MA (US)

( * ) Notice: Subject to any disclaimer, the term of this patent is extended or adjusted under 35 U.S.C. 154(b) by 304 days.

This patent is subject to a terminal disclaimer.

(21) Appl. No.: 10/659,617

(22) Filed: Sep. 10, 2003

(65) Prior Publication Data

US 2004/0059230 A1 Mar. 25, 2004

Related U.S. Application Data

(63) Continuation of application No. 10/081,574, filed on Feb. 21, 2002, now Pat. No. 6,695,789.

(51) Int. Cl.
*A61B 5/02* (2006.01)

(52) U.S. Cl. ...................................... 600/500; 600/485

(58) Field of Classification Search ................ 600/503, 600/485, 500
See application file for complete search history.

(56) References Cited

U.S. PATENT DOCUMENTS

| | | | |
|---|---|---|---|
| 4,260,951 A | 4/1981 | Lewyn | |
| 4,305,401 A * | 12/1981 | Reissmueller et al. | 600/503 |
| 4,307,727 A | 12/1981 | Haynes | |
| 4,632,121 A * | 12/1986 | Johnson et al. | 600/372 |
| 4,664,126 A | 5/1987 | Link | |
| 4,699,151 A | 10/1987 | Link | |
| 4,712,563 A | 12/1987 | Link | |
| 4,799,491 A | 1/1989 | Eckerle | |
| 4,830,017 A | 5/1989 | Perry et al. | |
| 4,836,213 A | 6/1989 | Wenzel et al. | |
| 4,928,702 A | 5/1990 | Cousin | |
| 5,025,792 A | 6/1991 | Hon et al. | |
| 5,033,471 A | 7/1991 | Yokoe et al. | |
| 5,218,967 A | 6/1993 | Shinomiya et al. | |
| 5,238,000 A | 8/1993 | Niwa | |
| 5,240,007 A | 8/1993 | Pytel et al. | |
| 5,243,992 A | 9/1993 | Eckerle et al. | |
| 5,247,944 A | 9/1993 | Hirano et al. | |
| 5,253,648 A | 10/1993 | Walloch | |
| 5,284,150 A | 2/1994 | Butterfield et al. | |
| 5,450,852 A | 9/1995 | Archibald et al. | |
| 5,640,964 A | 6/1997 | Archibald et al. | |
| 5,642,733 A | 7/1997 | Archibald et al. | |
| 5,649,542 A * | 7/1997 | Archibald et al. | 600/485 |
| 5,720,292 A | 2/1998 | Poliac | |
| 5,722,414 A | 3/1998 | Archibald et al. | |
| 5,738,103 A | 4/1998 | Poliac | |
| 5,749,366 A | 5/1998 | Odagiri et al. | |
| 5,779,630 A | 7/1998 | Fein et al. | 600/323 |

(Continued)

*Primary Examiner*—Charles A Marmer, II
*Assistant Examiner*—Patricia C. Mallari
(74) *Attorney, Agent, or Firm*—Altera Law Group, LLC

(57) ABSTRACT

A sensor interface assembly is used with a blood pressure measurement device to determine blood pressure of an underlying artery. The sensor interface assembly includes a base unit, a sensing unit and means for detachably connecting the sensing unit to the base unit. The base unit is pivotally attached to the blood pressure measurement device. The sensing unit includes sensing means for sensing blood pressure of each pulse as each pulse travels beneath the sensing means. The means for detachably connecting mechanically and electrically couple the sensing unit to the base unit.

9 Claims, 7 Drawing Sheets

U.S. PATENT DOCUMENTS

| | | |
|---|---|---|
| 5,797,850 A | 8/1998 | Archibald et al. .......... 600/494 |
| 5,832,924 A | 11/1998 | Archibald et al. |
| 5,908,027 A | 6/1999 | Butterfield et al. |
| 5,941,828 A * | 8/1999 | Archibald et al. .......... 600/494 |
| 6,081,742 A * | 6/2000 | Amano et al. .............. 600/513 |
| 6,159,157 A | 12/2000 | Archibald et al. .......... 600/485 |
| 6,241,679 B1 | 6/2001 | Curran ....................... 600/485 |
| 6,695,789 B1 * | 2/2004 | Thede et al. ................ 600/494 |

* cited by examiner

DISPOSABLE NON-INVASIVE BLOOD PRESSURE SENSOR

CROSS-REFERENCE TO RELATED APPLICATION(S)

This application is a continuation of U.S. patent application Ser. No. 10/081,574, filed Feb. 21, 2002, entitled "Disposable Non-Invasive Blood Pressure Sensor" by Roger C. Thede and Kevin R. Evans.

BACKGROUND OF THE INVENTION

The present invention relates to systems and devices for measuring arterial blood pressure. In particular, the invention relates to a two-piece sensor interface assembly for a non-invasive blood pressure measurement device, including a disposable sensing unit.

There has been a continuing need for devices which will measure blood pressure non-invasively and have accuracy comparable to invasive methods. Medwave, Inc. the assignee of the present invention, has developed non-invasive blood pressure measurement devices which are described in the following United States patents: U.S. Pat. No. 5,450,852 entitled CONTINUOUS NON-INVASIVE PRESSURE MONITORING SYSTEM; U.S. Pat. No. 5,640,964 entitled WRIST MOUNTED BLOOD PRESSURE SENSOR; U.S. Pat. No. 5,642,733 entitled BLOOD PRESSURE SENSOR LOCATOR; U.S. Pat. No. 5,649,542 entitled CONTINUOUS NON-INVASIVE BLOOD PRESSURE MONITORING SYSTEM; U.S. Pat. No. 5,720,292 entitled BEAT ONSET DETECTOR; U.S. Pat. No. 5,722,414 entitled CONTINUOUS NON-INVASIVE BLOOD PRESSURE MONITORING SYSTEM; U.S. Pat. No. 5,738,103 entitled SEGMENTED ESTIMATION METHOD; U.S. Pat. No. 5,797,850 entitled METHOD AND APPARATUS FOR CALCULATING BLOOD PRESSURE OF AN ARTERY; U.S. Pat. No. 5,941,828 entitled HAND-HELD NON-INVASIVE BLOOD PRESSURE MEASUREMENT DEVICE; U.S. Pat. No. 6,159,157 entitled BLOOD PRESSURE MEASUREMENT DEVICE WITH SENSOR LOCATOR; and U.S. Pat. No. 6,241,679 entitled NON-INVASIVE BLOOD PRESSURE SENSING DEVICE AND METHOD USING TRANSDUCER WITH ASSOCIATE MEMORY.

As described in these patents, the Medwave non-invasive blood pressure measurement device determines blood pressure by sensing pressure waveform data derived from an artery. As varying pressure is applied to the artery by a sensing chamber, pressure waveforms are sensed by a transducer to produce sensed pressure waveform data. The varying pressure maybe applied automatically in a predetermined pattern, or may be applied manually in a somewhat random fashion. The sensed pressure waveform data is analyzed to determine waveform parameters which relate to the shape of the sensed pressure waveforms. One or more blood pressure values are derived based upon the waveform parameters. The Medwave blood pressure measurement devices include both automated devices for continuously monitoring blood pressure (such as in a hospital setting) and hand-held devices which can be used by a physician, or by a patient when desired. These devices represent an important improvement in the field of non-invasive blood pressure measurement.

The non-invasive blood pressure measurement device is typically comprised of a housing unit with a sensor interface assembly attached thereto. The sensor interface assembly includes electrical circuitry, sensing means, including a transducer, and means for applying variable pressure to the artery. The sensor interface assembly is expensive to manufacture and in particular, the most expensive cost associated with it is the electrical circuitry. A problem arises in the hospital, or a clinical setting, where multiple patients use a limited number of non-invasive blood pressure measurement devices. When the sensor interface assembly becomes contaminated or damaged, it is expensive to have it replaced. Therefore, a sensor interface assembly is needed that is less expensive to replace in the non-invasive measurement device.

BRIEF SUMMARY OF THE INVENTION

The present invention relates to a non-invasive blood pressure measurement device for determining blood pressure of an artery. The device comprises a housing unit, a base unit and a sensing unit. The base unit is pivotally connected to the housing unit. The base unit includes electrical circuitry, a flexible ring, and a receptacle. The sensing unit includes a pressure transducer for sensing pulses of the underlying artery having a sensing surface, a flexible diaphragm having an active portion for transmitting blood pressure pulses of the underlying artery, interface means coupled between the sensing surface of the transducer and the flexible diaphragm for transmitting the blood pressure pulses within the underlying artery from the flexible diaphragm to the sensing surface of the transducer, a compressible ring, and connection means for detachably connecting the sensing unit to the receptacle of the base unit.

DETAILED DESCRIPTION

Figure 1:
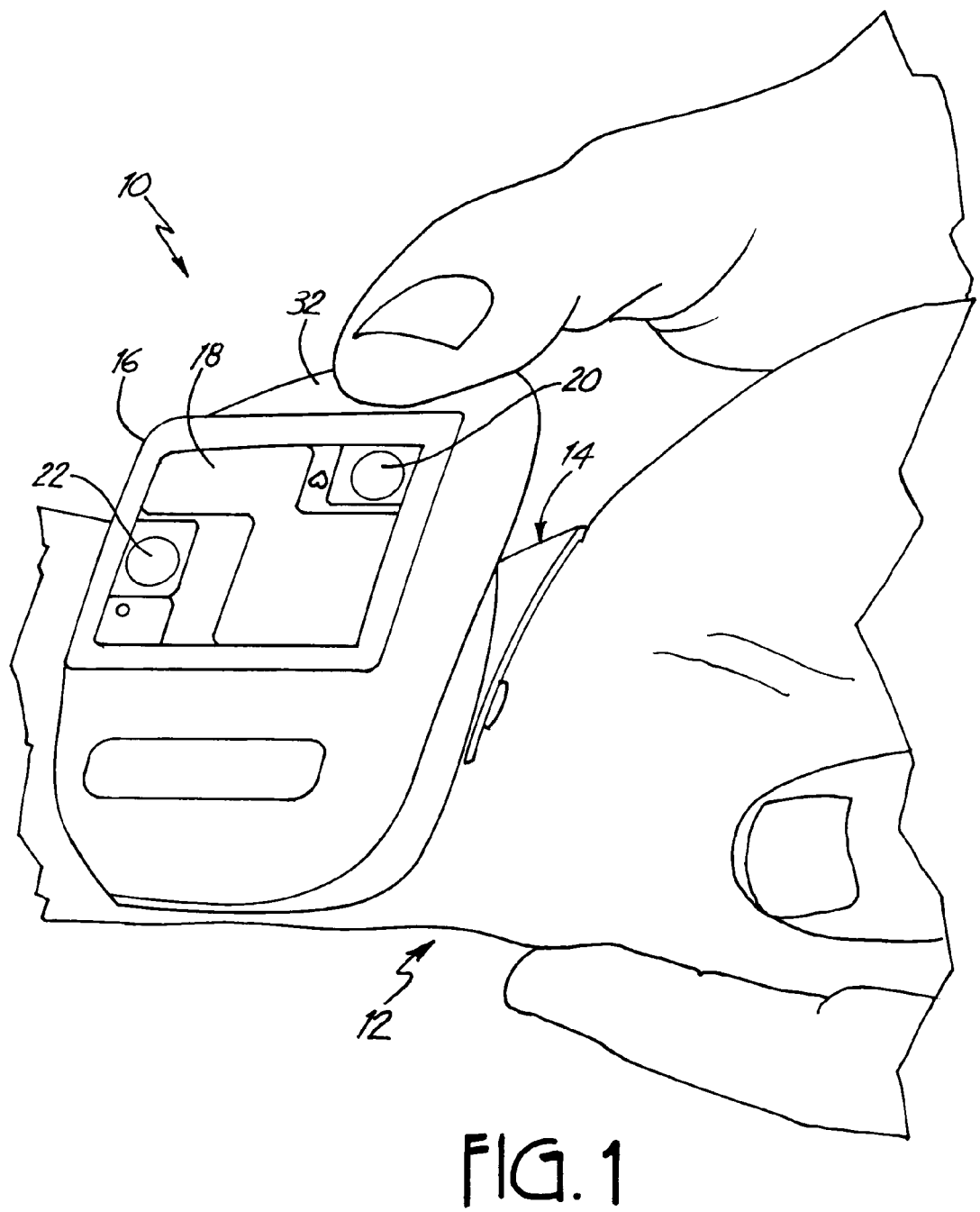
FIG. 1 is a perspective view of a blood pressure measurement device of the present invention positioned over a wrist of a patient.

FIG. 1 illustrates a blood pressure measurement device 10 being used to measure and display blood pressure within an underlying artery within a wrist 12 of a patient. Using a placement guide 14 of measurement device 10, measurement device 10 is placed at the projection of the styloid process bone perpendicular to wrist 12. With device 10, a small amount of force is applied to the radial artery, which runs along the styloid process bone. As the force is applied, blood pressure waveforms are recorded and the corresponding hold down pressure which is being manually applied is also recorded. Using the pressure shape of the blood pressure waveforms, waveform parameters are generated. These parameters, along with universal coefficients determined from clinical samples, are used to calculate pressure values which can then be displayed. Blood pressure measurement device 10 includes placement guide 14, a housing unit 16, a display panel 18, a patient identification toggle 20, a power switch 22, a sensor interface assembly 24 (shown in FIG. 2), including a base unit 26 and a sensing unit 28, and a connection assembly 30 (also shown in FIG. 2) between base unit 26 and housing unit 16.

Housing unit 16 contains the electrical components of measurement device 10. Placement guide 14 is connected to housing unit 16 at the base of housing unit 16. Placement guide 14 straddles the styloid process bone, automatically placing sensing unit 28 over the underlying artery. The shape and configuration of housing unit 16 allows it to hang on the patient's wrist, using placement guide 14 as a type of hook. Housing unit 16 includes a pressure platform 32, which is a flattened depression directly above sensor interface assembly 24. In operation, the user (medical personnel) applies pressure on pressure platform 32 with a thumb or finger. The hold-down force from the user's thumb applies a force in an axial direction (i.e., axial direction with respect to a central cylindrical axis of sensor interface assembly 24) to wrist 12 of the patient. The axial force is transmitted from pressure platform 32 of housing unit 16 to sensor interface assembly 24.

Patient identification toggle 20 is used to organize the recorded blood pressure information with respect to a particular patient. After actuating power switch 22, the user selects the specific patient for which blood pressure will be measured by pressing patient identification toggle 20. In one embodiment, display panel 18 displays a patient identification number for the currently selected patient. The patient identification number changes as patient identification toggle 20 is pressed. In one embodiment the user can scroll through a list of 16 patient identification memory locations.

Power switch 22 is actuated to turn on power to the circuitry within housing unit 16. Timing circuitry within housing unit 16 automatically turns power off after a predetermined period of inactivity. Actuation of switch 22, after the unit is turned on, causes display panel 18 to indicate previous readings of blood pressure and pulse rate.

Figure 2:
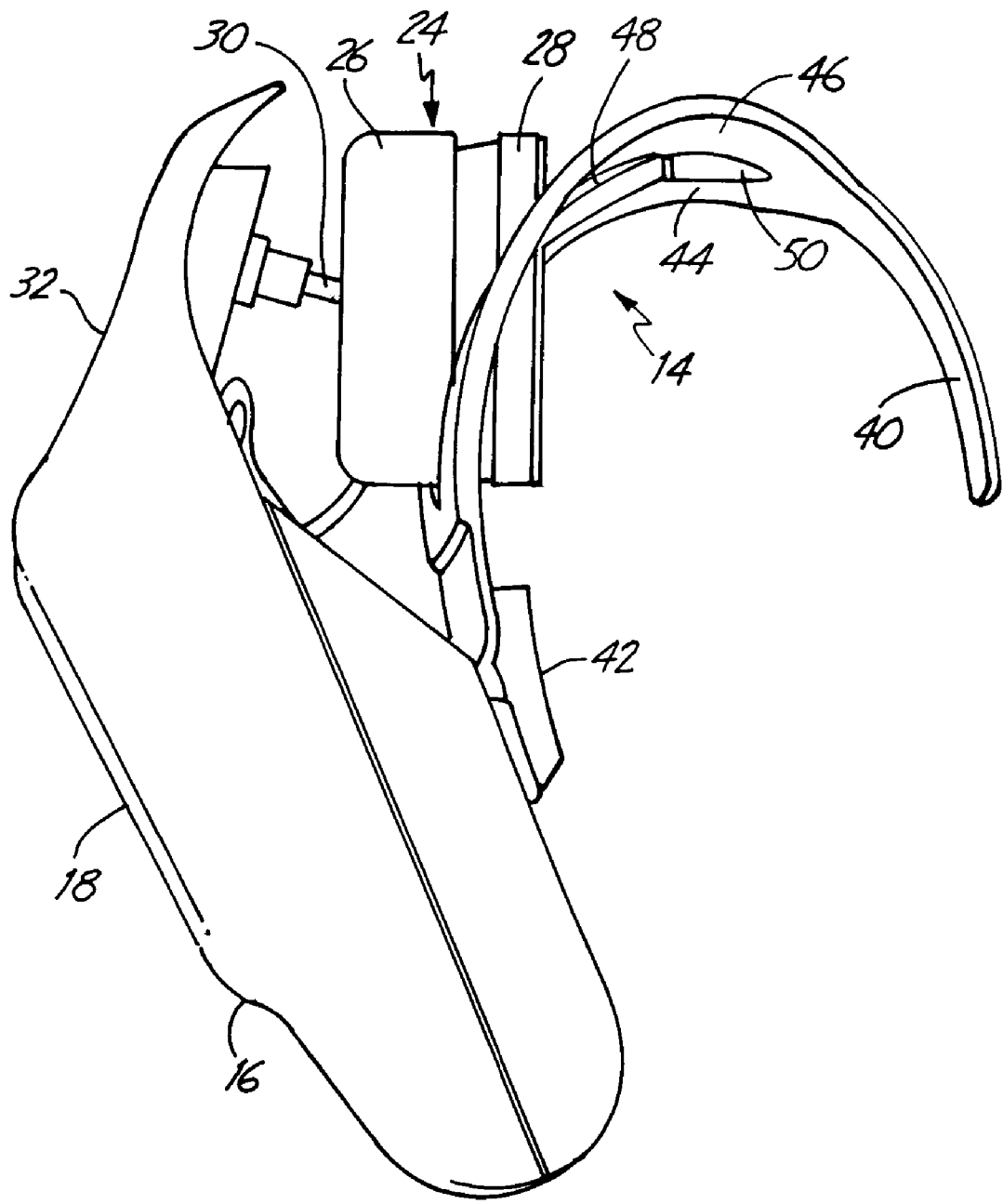
FIG. 2 is a side view of the blood pressure measurement device of FIG. 1.

FIG. 2 is a side view of blood pressure measurement device 10 showing sensor interface assembly 24 connected to housing unit 16. Sensor interface assembly 24 provides external measurements of blood pressure in an underlying artery. Sensor interface assembly 24 senses blood pressure non-invasively, thus blood pressure is measured at a lower cost and without medical risks. Since sensor interface assembly 24 is relatively small compared to the larger cuffs used with oscillometric and auscultatory methods, sensor interface assembly 24 applies a hold down pressure to only a relatively small area above the underlying artery of the patient. Consequently, blood pressure measurements may be taken with less discomfort to the patient. Because sensor interface assembly 24 does not require inflation or deflation, faster, more frequent measurements may be taken. Furthermore, sensor interface assembly 24 better conforms to the anatomy of the patient so as to be more comfortable to the patient and achieve more consistent and accurate blood pressure measurements.

Base unit 26 is pivotally connected to housing unit 16 by connection assembly 30 and sensing unit 28 is detachably connected to base unit 26. Connection assembly 30 allows sensor interface assembly 24 to pivot near the wrist surface to accommodate the anatomy of the patient. Because base unit 26 is pivotally coupled to the housing unit about a low pivot point, sensor interface assembly 24 is permitted to be stably positioned above the underlying artery. In addition, the low pivot point enables the user to apply a more direct, uniform force on sensing unit 28 (as discussed below). Thus, the hold down pressure is more uniformly applied to the anatomy above the underlying artery. As pressure is applied by housing unit 16 toward the artery, that force is transferred from housing unit 16, through connection assembly 30 to base unit 26, to sensing unit 28.

Figure 3:
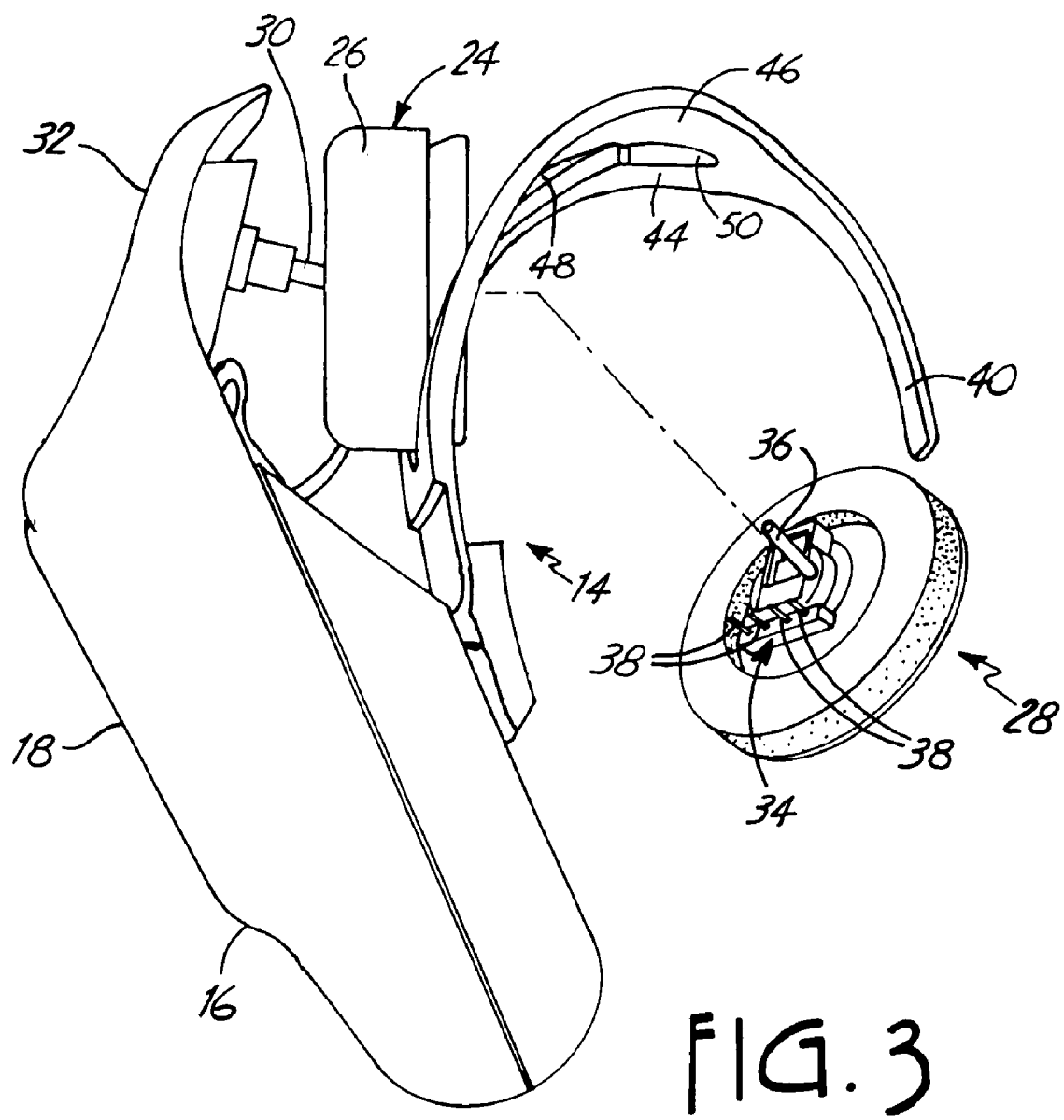
FIG. 3 is a side view of the blood pressure measurement device with a sensing unit detached from a sensor interface assembly.

FIG. 3 is a side view of blood pressure measurement device 10 with sensing unit 28 detached from base unit 26. Sensing unit 28 includes a connection means 34 for detachably connecting sensing unit 28 to base unit 26. Connection means 34 also provides an electrical connection between the two units. Connection means 34 is preferably comprised of an alignment element 36 and electrical connectors 38. Alignment element 36 and electrical connectors 38 are received by a receptacle (not shown) in base unit 26 (as discussed below). Alignment element 36 is used to precisely position electrical connectors 38 within base unit 26.

As seen by FIGS. 2 and 3, placement guide 14 is preferably a U-shaped member defined by the integral mold of hook 40, locator pad 42 and guide ribs 44 and 46. Opening 48 is a generally circular aperture that has a notch 50 near hook 40. Guide ribs 44 and 46 encircle opening 48 and notch 50, and meet at the base of hook 40.

When device 10 is placed on the patient, pad 42 contacts the palm side of the wrist of the patient, while hook 40 wraps around the backside of the wrist. Placement guide 14 is made of a flexible plastic so as to fit all patients, with the styloid process bone fitting into notch 50 of opening 48. Opening 48 also allows sensor interface assembly 24 to come in contact with the patient's wrist. Pad 42 becomes a pivot point about which force is applied.

Relying on a cantilever type action, device 10 allows the user to apply a force at pressure platform 32 of housing unit 16. Housing unit 16 pivots about pad 42, and sensor interface assembly 24 applies an axial force to the underlying artery.

Device 10, with placement guide 14 and the cantilever type action, allows sensor interface assembly 24 to be consistently placed in the proper position, and the hold-down force to be consistently applied in the axial direction with respect to wrist 12. Instead of having to palpate wrist 12 to identify the location of the radial artery, a user simply places device 10 adjacent wrist 12 so that placement guide 14 hooks onto the patient's wrist with guide ribs 44 and 46 straddling the projection of the styloid process bone. Placement guide 14 and the cantilever type action greatly simplifies the procedure of applying pressure by the user, because the user no longer controls the direction and angle at which pressure is applied with respect to the patient's wrist. The force applied to the artery is swept in an increasing fashion so the pressure waveform data from a series of pulses are obtained with different amounts of force being applied. To achieve the desired pattern of variable force, user feedback is preferably provided with device 10.

In an embodiment where the user applies pressure, feedback is in the form of a visual counter on display panel 18. As the user begins to apply pressure, a number is displayed corresponding to the amount of pressure applied by the user.

As the user increases the applied pressure, the displayed number proportionally increases. The user (medical personnel or patient) is previously instructed to increase pressure smoothly so that the displayed counter increases one integer at a time, approximately one per second. If the user increases the hold-down pressure too quickly, the displayed counter will also jump quickly through the corresponding numbers to indicate the choppy applied pressure. The user applies greater pressure until device 10 shows the resulting blood pressure measurements on display panel 18. Alternatively, the feedback to the user can be audible tones and/or visual movable bars. The process of applying force in response to audible tones and/or visual movable bars on display panel 18 is fully described in U.S. Pat. No. 5,941,828, entitled "Non-Invasive Blood Pressure Sensor With Motion Artifact Reduction", which is incorporated herein.

After the measurement, the user can then view the blood pressure reading. In a preferred embodiment, display panel 18 provides a digital readout of systolic and diastolic blood pressure, as well as pulse rate. An indication of memory location (by number) corresponding to the patient is also displayed. As soon as the reading is complete, device 10 is ready to take another reading. There is no need to clear display panel 18. Device 10 stores a predetermined number of previous readings (such as the last 10 readings). To review prior readings, patient identification toggle 20 or power switch 22 is pressed to cause a different reading from memory to be displayed on display panel 18.

Measurement device 10 also includes an external connector (not shown) which is a five pin connector that is used to transmit and receive data, recharge a battery (not shown) contained within housing unit 16 and provide an alternative power source to device 10. The external connector allows device 10 to be connected to a docking station (not shown) so that its internal battery can be recharged, and the collected blood pressure information can be downloaded to a central system. Device 10 can be used by a nurse or other employee in a hospital setting to collect blood pressure and heart rate information from a series of patients.

After blood pressure and heart rate data are obtained, the nurse places device 10 into a docking station coupled to a central computer (not shown), which can transmit a command via the external connector to device 10. In response, device 10 outputs blood pressure and heart rate information, already organized with respect to particular patients (with the patient identification toggle 19), via the external connector. Concurrently, the rechargeable battery within device 10 is being recharged, and power is supplied to device 10 from the docking station or central computer via the external connector, while device 10 is in the docking station. The central computer can then maintain a central database for all of the patients in the hospital, with the heart rate and blood pressure information automatically being downloaded into the database from device 10.

Figure 4A:
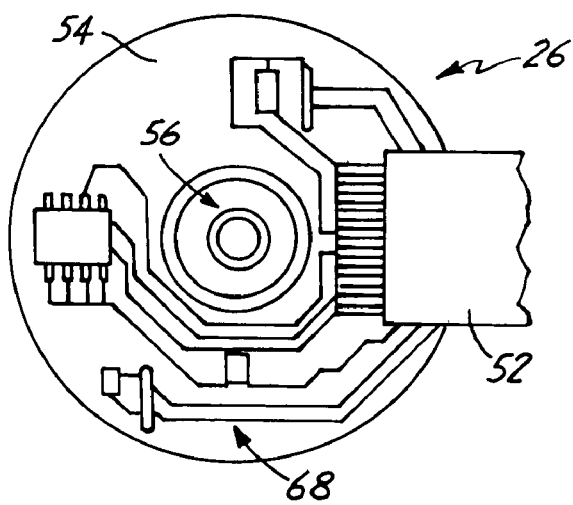
FIG. 4A is a top view of a base unit of the blood pressure measurement device.
Figure 4B:
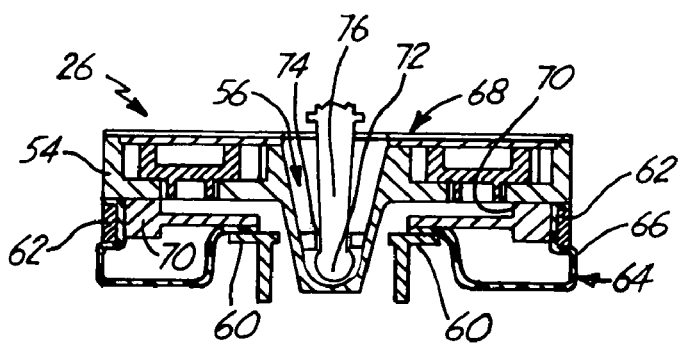
FIG. 4B is a sectional view of the base unit of the blood pressure measurement device.
Figure 4C:
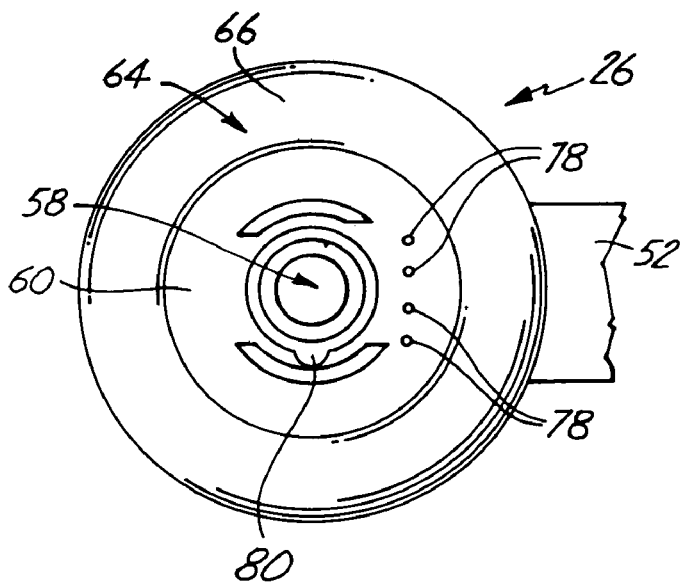
FIG. 4C is a bottom view of the base unit of the blood pressure measurement device.

FIGS. 4A–4C show top, sectional, and bottom views, respectively, of base unit 26 of blood pressure measurement device 10. Base unit 26 includes an electrical connector 52, a top plate 54, an upper receptacle 56, a lower receptacle 58, an inner mounting ring 60, an outer mounting ring 62, a flexible ring 64 comprised of a side wall diaphragm 66, electrical circuitry 68 and an upper capture 70.

Electrical connector 52 electrically couples base unit 26 with housing unit 16. Additionally, power for sensing unit 28 is delivered via electrical connector 52.

Base unit 26 is pivotally connected to housing unit 16 by connection assembly 30 (as seen in FIGS. 2 and 3). Connection assembly 30 is preferably comprised of a ball 72 and a socket 74 arrangement. Ball 72 is located at a lower end of a stem 76 of connection assembly 30 extending from housing unit 16. Socket 74 is formed within a lower portion of upper receptacle 56 of base unit 26. Ball 72 is pivotally mounted in socket 74 to connect base unit 26 to housing unit 16.

Figure 5A:
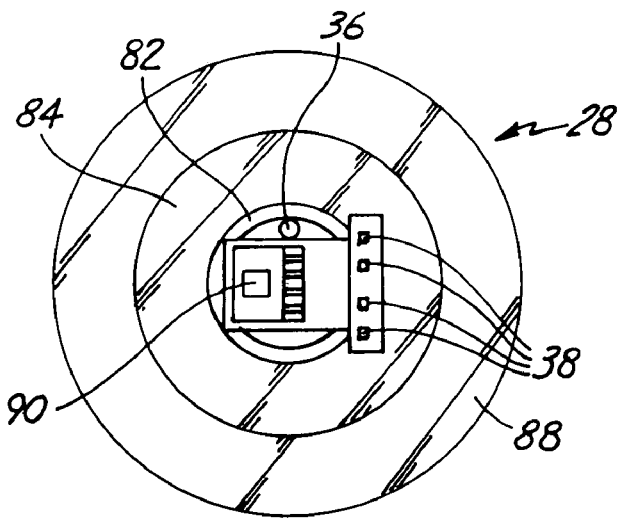
FIG. 5A is a top view of the sensing unit of the blood pressure measurement device.

Sensing unit 28 is detachably connected to base unit 26 by connection means 34 (shown in FIGS. 3 and 5A). Connector receptacles 78 and an alignment receptacle 80 are located in base unit 26 for receiving connection means 34. Preferably, connector receptacles 78 and alignment receptacle 80 are located in inner mounting ring 60 of lower receptacle 58.

Flexible ring 64 is defined by side wall diaphragm 66 and upper capture 70. Side wall diaphragm 66 is formed from a generally circular sheet of flexible material, such as polyurethane, and is preferably filled with fluid. Diaphragm 66 bulges outward when flexible ring 64 is filled with fluid. The outer edge portion of diaphragm 66 is held between top plate 54, outer ring 62 and upper capture 70. The inner edge portion of diaphragm 66 is held between inner ring 60 and upper capture 70. Ring 64 is compressible and expandable in the vertical direction so as to be able to conform to the anatomy of the patient surrounding the underlying artery. As a result, the distance between top plate 54 and the patient's anatomy can vary around the periphery of flexible ring 64 according to the contour of the patient's anatomy. Furthermore, because fluid is permitted to flow through and around ring 64, pressure is equalized around the patient's anatomy.

Figure 5B:
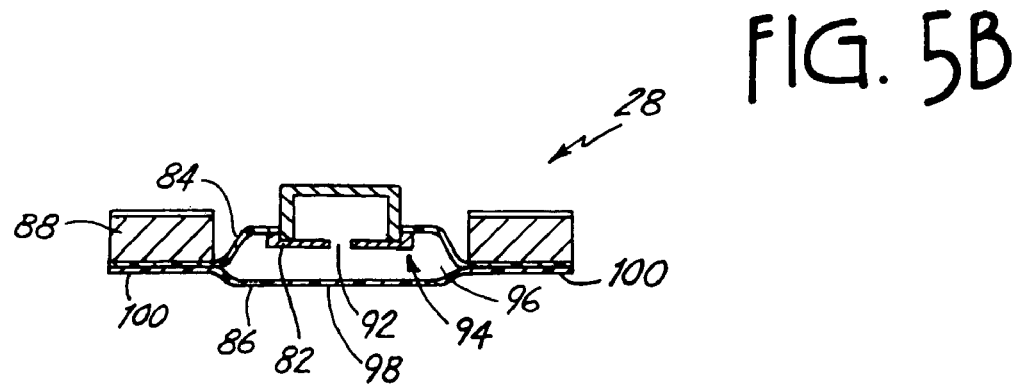
FIG. 5B is a sectional view of the sensing unit of the blood pressure measurement device.
Figure 5C:
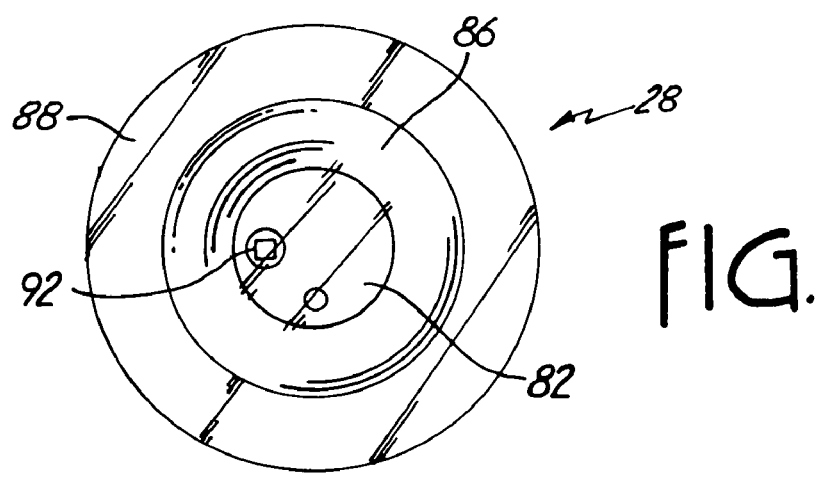
FIG. 5C is a bottom view of the sensing unit of the blood pressure measurement device.

FIGS. 5A–5C show top view, sectional and bottom views, respectively, of sensing unit 28 of blood pressure measurement device 10. Sensing unit 28 includes a diaphragm capture 82, an inner diaphragm 84, a flexible (or outer) diaphragm 86, a compressible ring 88, a pressure transducer 90 having a sensing surface 92, and connection means 34. Inner diaphragm 84 and flexible diaphragm 86 form a sensor chamber 94 which is filled with a fluid coupling medium 96.

Connection means 34 is preferably comprised of alignment element 36 and electrical connectors 38. Electrical connectors 38 are connected to and extend from pressure transducer 90. Electrical connectors 38 are received by connector receptacles 78 (not shown) located on base unit 26. Electrical connectors 38 provide the connection between transducer 90 and the electrical circuitry of base unit 26. Alignment element 36 is received by alignment receptacle 80 (not shown) of base unit 26 to precisely position electrical connectors 38 within the corresponding connector receptacles of base unit 26. As seen in FIG. 3, sensing unit 28 can be individually detached from base unit 26 (and thereby housing unit 16) and replaced by another sensing unit.

Compressible ring 88 is generally annular and is preferably formed from a foam rubber or other pulse dampening material, such as open cell foam or closed cell foam. Ring 88 is centered about flexible diaphragm 86 and positioned above diaphragms 84 and 86. Compressible ring 88 is isolated from fluid coupling medium 96 within sensor chamber 94 formed by diaphragms 84 and 86. The compressibility of ring 88 allows ring 88 to absorb and dampen forces in a direction parallel to the underlying artery. The forces are exerted by the blood pressure pulses on sensing unit 28 as the blood pressure pulses cross flexible diaphragm 86. Because compressible ring 88 is isolated from fluid coupling medium 96, the forces absorbed or received by ring 88 cannot be transmitted to fluid coupling medium 96. Instead, these forces are transmitted across compressible ring 88 and flexible ring 64 to top plate 54 (shown in FIG. 4B), which is a path distinct and separate from fluid coupling medium 96.

Rings 64 and 88 apply force to the anatomy of the patient to neutralize the forces exerted by tissue surrounding the underlying artery. Rings 64 and 88 are compressible in height, thus the height of the side wall of sensor interface assembly 24 will decrease as it is pressed against the patient.

Inner diaphragm 84 is an annular sheet of flexible material having an inner diameter sized to fit around diaphragm capture 82. An inner portion of inner diaphragm 84 is trapped or captured, and preferably adhesively affixed, to the lip of diaphragm capture 82. Inner diaphragm 84 is permitted to initially move upward as flexible diaphragm 86 conforms to the anatomy of the patient surrounding the underlying artery. As compressible ring 88 is pressed against the anatomy of the patient surrounding the artery to neutralize or offset forces exerted by the tissue, flexible diaphragm 86 is also pressed against the anatomy and the artery. However, because inner diaphragm 84 is permitted to roll upward, sensor chamber 94 does not experience a large volume decrease or a large corresponding pressure increase. Thus, sensor interface assembly 24 permits greater force to be applied to the anatomy of the patient through compressible ring 88 to neutralize tissue surrounding the artery without causing a corresponding large, error-producing change in pressure within sensor chamber 94 as the height of the side wall changes and the shape of flexible diaphragm 86 changes. As a result, sensor interface assembly 24 achieves more consistent and accurate blood pressure measurements.

Flexible diaphragm 86 is a generally circular sheet of flexible material capable of transmitting forces from an outer surface to fluid coupling medium 96 within sensor chamber 94. Diaphragm 86 is coupled to inner diaphragm 84 and is configured for being positioned over the anatomy of the patient above the underlying artery. Diaphragm 86 includes an active portion 98 and a non-active portion 100 or skirt. Non-active portion 100 constitutes the area of diaphragm 86 where inner diaphragm 84 is heat sealed or bonded to diaphragm 86, preferably adjacent compressible ring 88. Active portion 98 of flexible diaphragm 86 is not bonded to inner diaphragm 84, and is positioned below and within the inner diameter of ring 88. Active portion 98 of diaphragm 86 is the active area of sensing unit 28 which receives and transmits pulse pressure to pressure transducer 90.

Fluid coupling medium 96 within sensor chamber 94 may consist of any fluid (gas or liquid) capable of transmitting pressure from flexible diaphragm 86 to transducer 90. Fluid coupling medium 96 interfaces between active portion 98 of diaphragm 86 and transducer 90 to transmit blood pressure pulses to transducer 90. Because fluid coupling medium 96 is contained within sensor chamber 94, which is isolated from compressible ring 88 of sensing unit 28, fluid coupling medium 96 does not transmit blood pressure pulses parallel to the underlying artery, forces from the tissue surrounding the underlying artery, and other forces absorbed by compressible ring 88 to transducer 90. As a result, sensing unit 28 more accurately measures and detects arterial blood pressure.

Sensing unit 28 of sensor interface assembly 24 permits accurate and consistent calculation of blood pressure. Because of the large sensing surface 92 through which blood pressure pulses may be transmitted to transducer 90, sensing unit 28 is not as dependent upon accurate positioning of active portion 98 of flexible diaphragm 86 over the underlying artery. Thus, sensor interface assembly 24 is more tolerant to patient movement as measurements are being taken.

Figure 6:
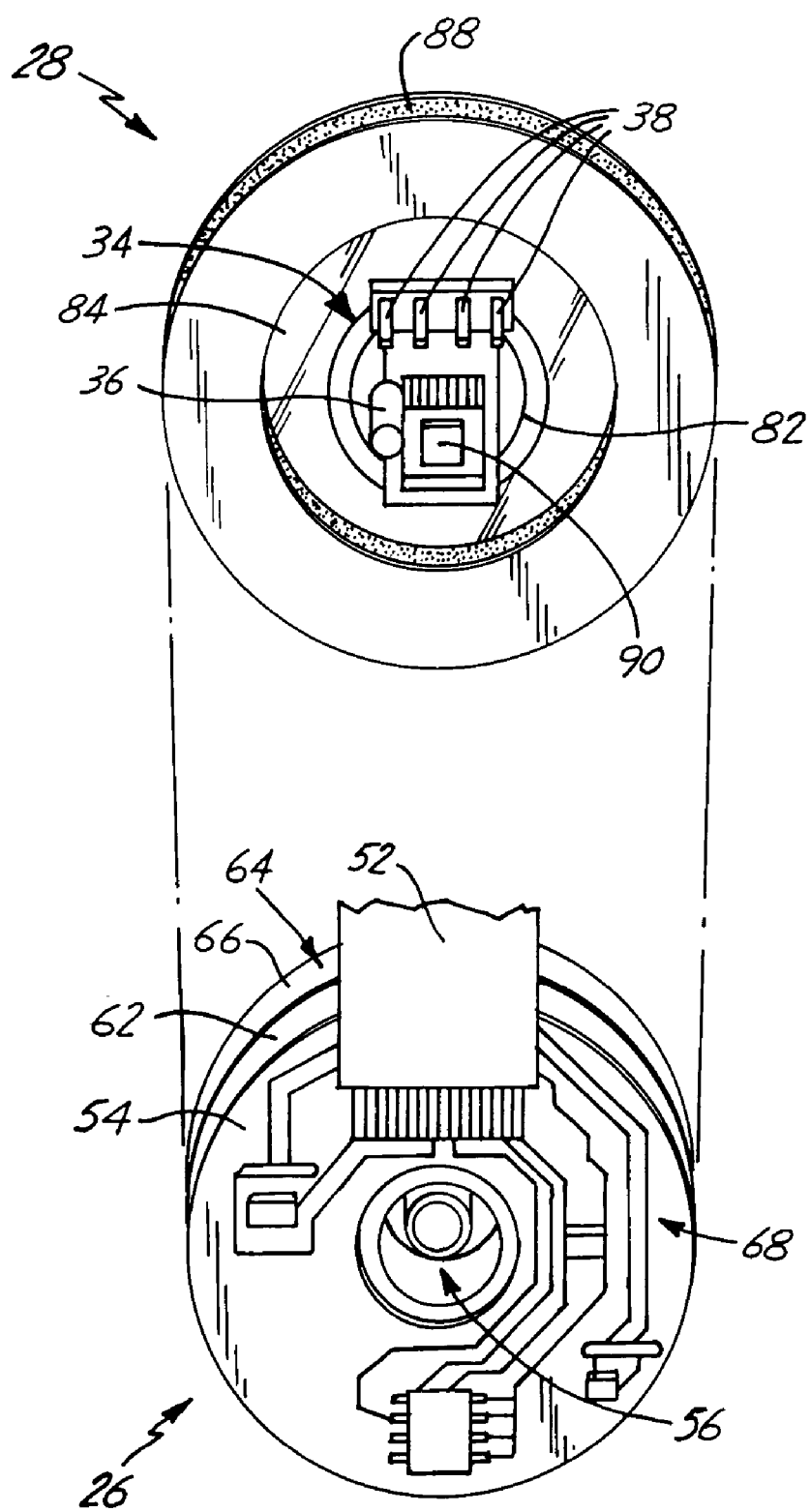
FIG. 6 is a top exploded view of the base unit and the sensing unit of the blood pressure measurement device.
Figure 7:
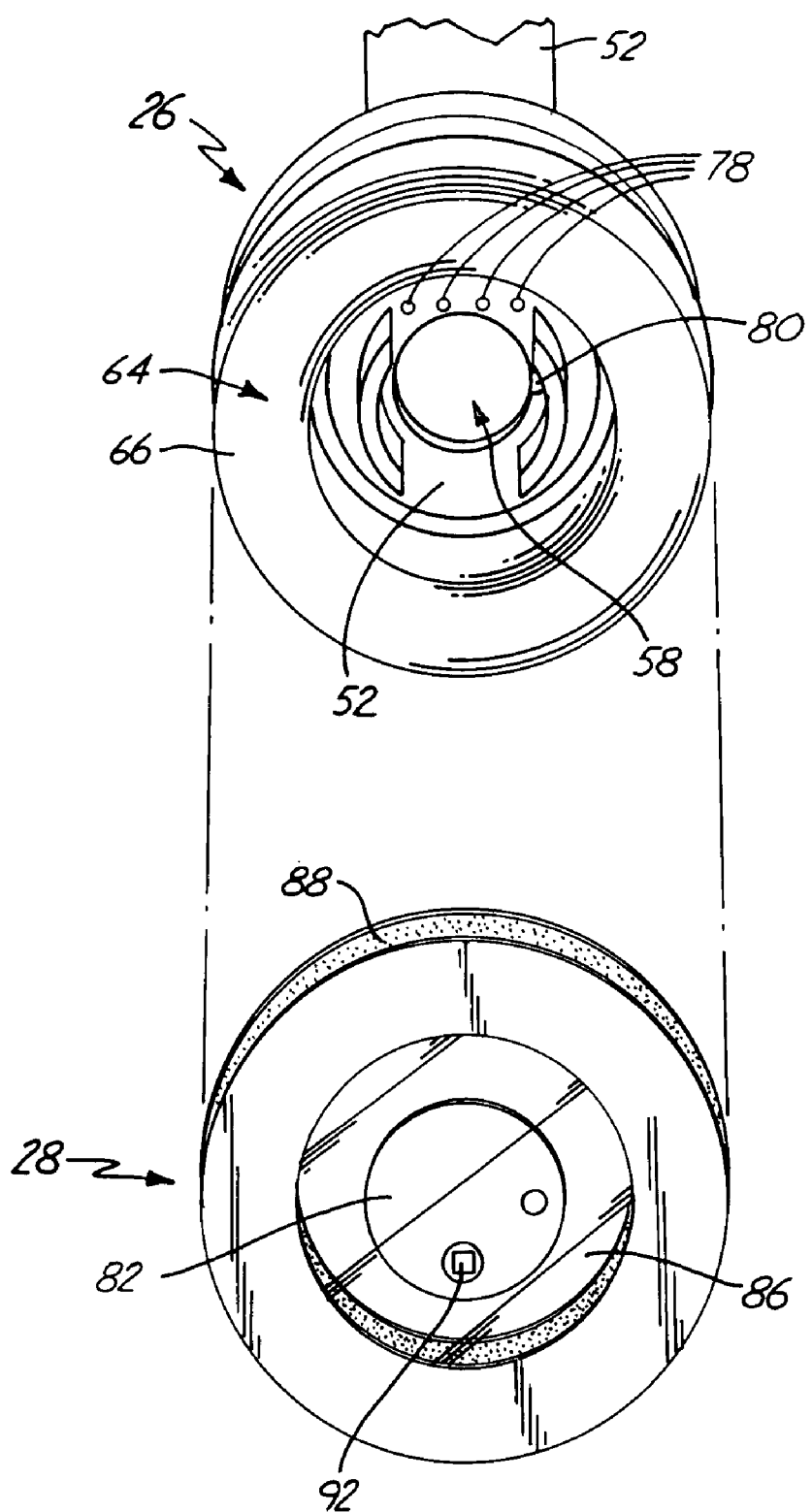
FIG. 7 is a bottom exploded view of the base unit and the sensing unit of the blood pressure measurement device.

FIG. 6 is a top exploded view of base unit 26 and sensing unit 28 and FIG. 7 is a bottom exploded view of base unit 26 and sensing unit 28. Base unit 26 includes electrical connector 52, top plate 54, upper receptacle 56, lower receptacle 58, inner mounting ring 60, outer mounting ring 62, flexible ring 64 comprised of a side wall diaphragm 66, and electrical circuitry 68. Sensing unit 28 includes diaphragm capture 82, inner diaphragm 84, flexible (or outer) diaphragm 86, compressible ring 88, pressure transducer 90 having sensing surface 92, and connection means 34. When assembled, flexible ring 64 and compressible ring 88 form the side wall of sensor interface assembly 24.

Connection means 34 of sensing unit 28 are used to detachably connect sensing unit 28 to base unit 26. Connection means 34 also provide an electrical connection between the two units. Connection means 34 extend from transducer 90 of sensing unit 28 and are received by lower receptacle 58 of base unit 26. Connection means 34 is preferably comprised of alignment element 36 and electrical connectors 38. Electrical connectors 38 are connected to and extend from pressure transducer 90. Electrical connectors 38 are received by corresponding connector receptacles 78 located within inner mounting ring 60 of lower receptacle 58. Electrical connectors 38 provide the connection between transducer 90 and electrical circuitry 68 of base unit 26. Alignment element 36 is used to precisely position electrical connectors 38 within connector receptacles 78 of base unit 26. Alignment element 36 of sensing unit 28 is received by alignment receptacle 80 within inner mounting ring 60 of lower receptacle 58. Proper alignment between sensing unit 28 and base unit 26 is needed for electrical connectors 38 to be connected at connector receptacles 78. Sensing unit 28 can be individually detached from base unit 26 (and thereby housing unit 16) and replaced by another sensing unit.

The blood pressure measurement devices of the present invention determine blood pressure values from the sensed waveform pressure amplitudes sensed by sensing unit 28 and from other parameters derived from the pressure amplitudes using a stored set of coefficients. Base unit 26 includes electrical circuitry 68 which transmits pressure data sensed by transducer 90 of sensing unit 28 to a microprocessor (not shown) in housing unit 16 (FIG. 1). The microprocessor determines the blood pressure values. Transducer 90 senses the pressure data transmitted from flexible diaphragm 86 through fluid coupling medium 96. Transducer 90 is connected to electrical circuitry 68 by electrical connectors 38. Transducer 90 is powered by and sends a signal producing output signal to the electrical circuitry 68 of base unit 26. The signal producing output signal corresponds to the sensed pressure data from transducer 90. Electrical circuitry 68 then transmits the signal producing output signal to the microprocessor through electrical connector 52.

Transducer 90 senses fluid pressure communicated to transducer 90 within sensing unit 28 and supplies an electrical signal through electrical connectors 38 to electrical circuitry 68. The sensed pressure data output of transducer 90 is typically an analog electrical signal representative of sensed pressure. The signal is amplified by an amplifier and applied to an input of an analog-to-digital converter. The A/D converter converts the analog signal to digital data which is transmitted to the electrical circuitry 68. Electrical circuitry 68 transmits the data to the microprocessor where a plurality of parameters are derived using the sensed pressure data received from transducer 90. The microprocessor determines a blood pressure value using the derived parameters, along with universal coefficients ascertained from clinical tests.

The blood pressure measurement device of the present invention calculates a systolic blood pressure value and a diastolic blood pressure value based upon the sensed pressure data transmitted by transducer 90. The blood pressure values are determined by using parameters derived from waveform pressure amplitudes based upon the sensed pressure data and coefficients obtained from clinical data. A pressure amplitude is determined at each sample point. The parameters may be calculated from shape characteristics of the waveform pressure amplitudes or parameters calculated from functions, such as curves based upon relationships between particular points of several waveforms. Once the parameters to be used in calculating blood pressure values are selected, coefficients corresponding to each parameter must be determined and applied. Coefficients represent the relationship between a particular parameter set and the resulting blood pressure value to be determined from that particular parameter set. Coefficients are initially ascertained from clinical tests upon patients having known blood pressure values. Each particular coefficient is preferably ascertained so as to be applicable for calculating blood pressure values from the derived waveform parameters of all patients. Alternatively, individualize coefficients may be used to calculate blood pressure values from derived waveform parameters of particular patients falling within a particular age group or other specialized groups.

Sensor interface assembly 24 achieves a zero pressure gradient across active portion 98 of the sensing unit 28, achieves a zero pressure gradient between transducer 90 and the underlying artery, attenuates or dampens pressure pulses that are parallel to sensing surface 92 of transducer 90, and neutralizes forces of the tissue surrounding the underlying artery. Sensor interface assembly 24 contacts and applies force to the anatomy of the patient across non-active portion 100 and active portion 98 of flexible diaphragm 86. However, the pressure within sensor chamber 94 is substantially equal to the pressure applied across active portion 98 of flexible diaphragm 86. In addition, because fluid coupling medium 96 within sensor chamber 94 is isolated from ring 88, pressure pulses parallel to the underlying artery, forces from tissue surrounding the underlying artery, and other forces absorbed by ring 88 are not transmitted through fluid coupling medium 96 to transducer 90. Consequently, sensor interface assembly 24 also achieves a zero pressure gradient between transducer 90 and the underlying artery. The remaining force applied by sensor interface assembly 24 across non-active portion 100, which neutralizes or offsets forces exerted by the tissue surrounding the underlying artery, is transferred through the side wall (rings 64 and 88) to top plate 54. As a result, the geometry and construction of sensor interface assembly 24 provides the proper ratio of pressures between non-active portion 100 and active portion 98 of flexible diaphragm 86 to neutralize tissue surrounding the underlying artery and to accurately measure the blood pressure of the artery.

Sensing unit 28 is detachably connected to base unit 26 such that sensing unit 28 may be replaced if contaminated or damaged. The blood pressure measurement device is typically used for non-invasively monitoring blood pressure in a hospital setting, by a physician or a patient. During use, the sensing unit 28, which contacts the patient's anatomy, may become contaminated or damaged. In addition, the blood pressure measurement device may be used by multiple patients within one facility. To lower the costs associated with the blood pressure measurement device, it is desirable to have a low cost solution which enables the use of a single device with multiple patients. The present invention serves this purpose. To avoid contamination between patients and for more efficient use of the device by multiple patients, sensing unit 28 is disposable and a new one is used for each patient. Sensing unit 28, including pressure transducer 90, is detachable from base unit 26. Sensing unit 28 of sensor interface assembly 24 has a lower manufacturing cost than base unit 26 because of the electrical circuitry associated with base unit 26. A disposable sensing unit 28 is desirable because it is less expensive to replace than an entire sensor interface assembly, including base unit 26. Therefore, upon contamination or damage to the sensor unit portion of sensor interface assembly 24, the base unit is retained while the sensing unit is disposed of and replaced.

Although the present invention has been described with reference to preferred embodiments, workers skilled in the art will recognize that changes may be made in form and detail without departing from the spirit and scope of the invention. For example, the present invention has been described for use with a device for manually applying hold down pressure to take blood pressure readings. However, the present invention is equally applicable to and intended to be used with devices that automatically apply hold down pressure.

The invention claimed is:

1. A sensor interface assembly for a blood pressure measurement device that determines blood pressure of an underlying artery, the sensor interface assembly comprising:
   a base unit for pivotally attaching to the blood pressure measurement device;
   a sensing unit including sensing means for sensing a blood pressure of each pulse as each pulse travels beneath the sensing means; and
   means for detachably connecting the sensing unit to the base unit wherein the means for detachably connecting mechanically and electrically couple the sensing unit to the base unit.

2. The sensor interface assembly of claim 1 wherein the means for detachably connecting comprises a plurality of electrical connectors connected to the sensing means, the connectors being received by a receptacle of the base unit.

3. The sensor interface assembly of claim 2 wherein the means for detachably connecting further comprises an alignment element for aligning the electrical connectors with the receptacle.

4. The sensor interface assembly of claim 2 wherein the electrical connectors provide power to the sensing unit and receive output signals from the sensing means.

5. The sensor interface assembly of claim 1 wherein the sensing means of the sensing unit includes:
   a pressure transducer having a sensing surface for sensing pulses of the underlying artery;
   a flexible diaphragm having an active portion for transmitting blood pressure pulses of the underlying artery; and
   interface means coupled between the sensing surface of the transducer and the flexible diaphragm for transmitting the blood pressure pulses within the underlying artery from the flexible diaphragm to the sensing surface of the transducer.

6. The sensor interface assembly of claim 1 wherein the base unit further comprises a flexible ring for equalizing pressure around the sensing means.

7. A sensor for a non-invasive blood pressure measurement device, the sensor for measuring blood pressure pulses within an underlying artery surrounded by tissue of a patient as the underlying artery is compressed, the sensor comprising:

a base unit for coupling to the blood pressure measurement device, the base unit including electrical circuitry, a flexible ring and a connection receptacle; and a sensing unit comprising:

a pressure transducer for sensing pulses of the underlying artery, the transducer having a sensing surface;

a flexible diaphragm having an active portion for transmitting blood pressure pulses of the underlying artery;

interface means coupled between the sensing surface of the transducer and the flexible diaphragm for transmitting the blood pressure pulses within the underlying artery from the flexible diaphragm to the sensing surface of the transducer;

a compressible ring; and connecting means for detachably connecting the sensing unit to the receptacle of the base unit.

8. A non-invasive blood pressure measurement device for determining blood pressure of an artery, the device comprising:

a housing unit;

a base unit pivotally coupled to the housing unit, the base unit including electrical circuitry interconnected with the housing unit; and a sensing unit for sensing pulses of the underlying artery, the sensing unit being detachably connected to the base unit;

wherein the sensing unit includes a plurality of electrical connectors which are received by a receptacle of the base unit to provide both electrical and mechanical connection of the sensing unit to the base unit; and wherein the electrical connectors provide power to the sensing unit and receive output signals from the sensing means.

9. The device of claim 8 wherein the sensing unit further includes an alignment element for aligning the electrical connectors with the receptacle.

* * * * *